(12) United States Patent
Kiedrowski

(10) Patent No.: US 8,634,149 B2  
(45) Date of Patent: Jan. 21, 2014

(54) SYSTEM TUBE AND PROCESS FOR SUPPORTING CYLINDRICAL ELEMENTS OF AN ENDOSCOPE OPTICAL SYSTEM

(75) Inventor: Gregor Kiedrowski, Hamburg (DE)

(73) Assignee: Olympus Winter & IBE GmbH, Hamburg (DE)

( * ) Notice: Subject to any disclaimer, the term of this patent is extended or adjusted under 35 U.S.C. 154(b) by 0 days.

(21) Appl. No.: 13/346,897

(22) Filed: Jan. 10, 2012

(65) Prior Publication Data  
US 2012/0176669 A1 Jul. 12, 2012

(30) Foreign Application Priority Data  
Jan. 10, 2011 (DE) .......... 10 2011 008 105

(51) Int. Cl.  
*G02B 7/02* (2006.01)

(52) U.S. Cl.  
USPC .......... 359/819; 359/811; 359/815

(58) Field of Classification Search  
USPC ......... 359/435, 503, 506, 808, 811, 815, 819, 359/830; 165/163  
See application file for complete search history.

(56) References Cited

U.S. PATENT DOCUMENTS

| | | | |
|---|---|---|---|
| 4,148,550 A * | 4/1979 | MacAnally | 359/435 |
| 6,201,649 B1 | 3/2001 | Rudischhauser et al. | |
| 6,398,723 B1 | 6/2002 | Kehr et al. | |
| 7,660,052 B2 | 2/2010 | Scholer | |
| 2008/0062540 A1 | 3/2008 | Scholer | |

* cited by examiner

*Primary Examiner* — Mahidere Sahle  
(74) *Attorney, Agent, or Firm* — Scully, Scott, Murphy & Presser, P.C.

(57) ABSTRACT

A system tube of an endoscope optical system, designed to contain cylindrical elements of an image guide provided with lenses and to support the elements by tongues cut out of the wall of the system tube and deformed nonelastically. Wherein the tongues are deformed toward the outside and are bent elastically by a holder toward the inside to below the level of the outer surface of the system tube. In a system tube of an endoscope optical system, designed to contain cylindrical elements of an image guide provided with lenses and to support the elements by means of nonelastically deformed tongues cut out of the wall of the system tube, the tongues are deformed toward the outside and are elastically bent by a holder toward the inside to below the level of the outer surface of the system tube.

11 Claims, 2 Drawing Sheets

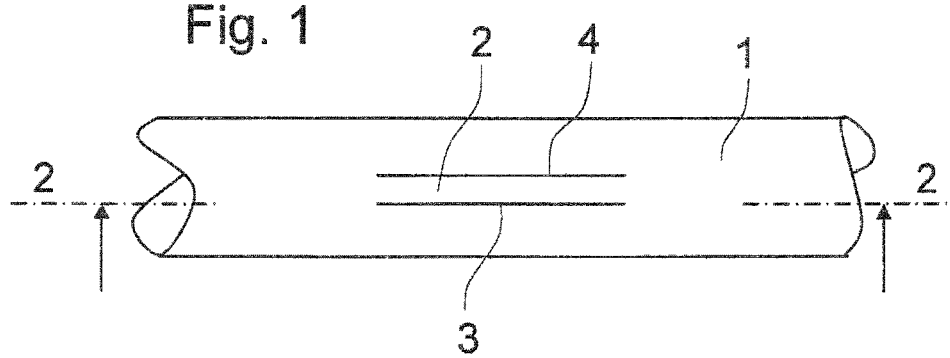
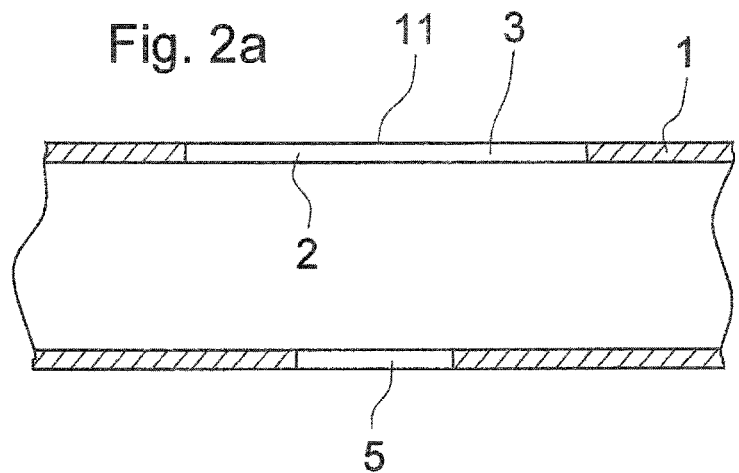
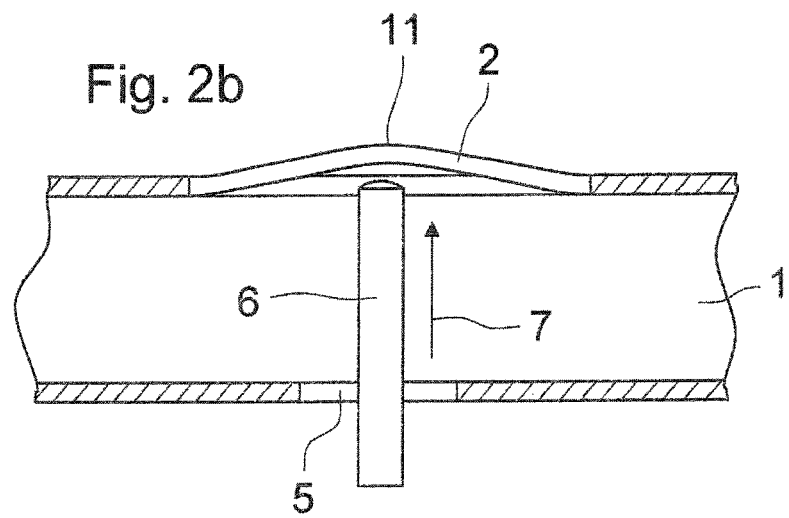

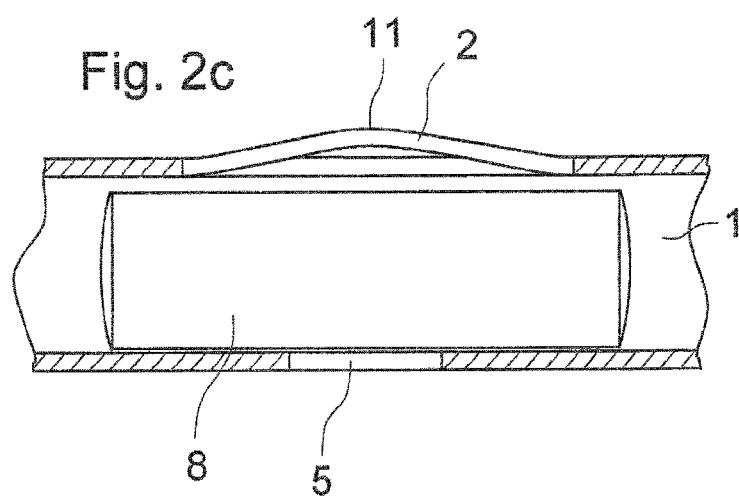
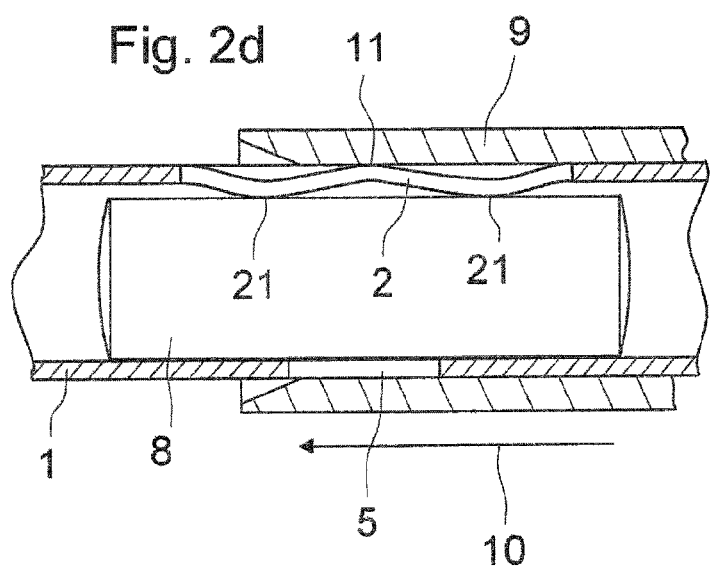
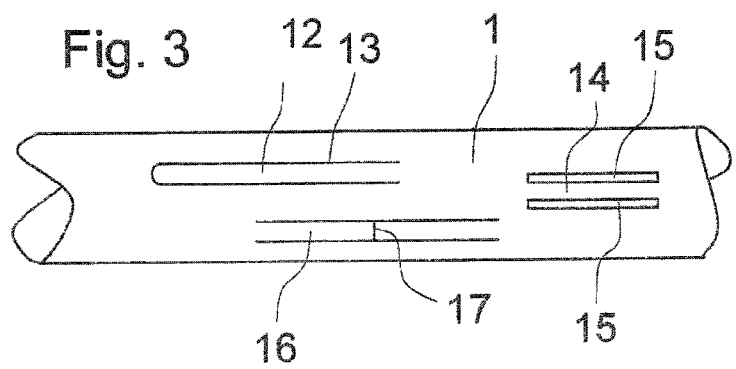

SYSTEM TUBE AND PROCESS FOR SUPPORTING CYLINDRICAL ELEMENTS OF AN ENDOSCOPE OPTICAL SYSTEM

CROSS-REFERENCE TO RELATED APPLICATION

The present application is based upon and claims the benefit of priority from DE 10 2011 008 105.4 filed on Jan. 10, 2011, the entire contents of which is incorporated herein by reference.

BACKGROUND

1. Field

The present invention generally relates to an endoscope optical system and more particularly to a system tube of an endoscope optical system and a process for retaining cylindrical elements.

2. Prior Art

An endoscope optical system has an image guide which transfers the image from a distally disposed objective to a proximally disposed viewing device, e.g., an ocular or a video camera. In designs of this class, the image guide is provided with lenses which are packed behind each other in a system tube, optionally with spacing tubes in between, and guided into the optically correct position by it (the system tube). The system tube usually consists of metal.

In this process it is necessary to make sure that the lenses are firmly retained in the system tube so that their position cannot change in case of shaking, which would lead to a disturbing jumping of the viewing direction.

In the case of system tubes of this type, tongues are cut out from the wall of the system tube and deformed nonelastically, permitting the reliable and solid support of the cylindrical elements of the image guide, thus the lenses and optionally also the spacers.

DE 10 2006 041 920 A1 shows a system tube of this type in which the tongues are deformed nonelastically toward the inside. This leads to a constriction of the free cross-section in the area of the tongues, by means of which cylindrical elements disposed in the system tube are reliably clamped or can be guided with low play. Securing of the image guide against rattling of its elements with resulting jumps in the image direction is achieved reliably. However, this known design also has considerable drawbacks. During the insertion of the elements of the image guide into the system tube, clamping forces must be overcome. This interferes with the fine adjustment of the elements. An additional considerable drawback occurs during disassembly, thus when the cylindrical elements of the image guide must be removed again from the system tube. They must then be slid with force from the area of the clamping tongues, which can lead to problems, e.g., to damage.

Patent DE 197 50 685 A1 shows a system tube of an endoscope optical system, wherein openings are provided in the wall of the system tube through which adhesive is introduced in the form of adhesive dots to retain the lenses disposed in the system tube.

DE 197 32 991 A1 shows a system tube in the wall of which beads are disposed, wherein the system tube is deformed toward the inside by these beads and thus lies adjacent to cylindrical elements disposed in the system tube.

The goal of the present invention consists of simplifying the assembly and disassembly of the elements of the image guide in a system tube of the relevant class.

SUMMARY

According to the invention the tongues are nonelastically deformed toward the outside, specifically such that they can be bent elastically towards the interior to below the level of the outer surface of the system tube, thus the level at which these lugs were positioned prior to the nonelastic deformation. The lugs are pressed in with any suitable holder, e.g., with the thumbs. Even if the point of the lug located farthest to the outside with regard to the axis of the system tube is exactly at the radial distance which it occupied prior to the nonelastic deformation, thus at the original level of the surrounding system tube, retention by clamping force of the cylindrical element, located at this point, a lens or a spacer tube located with the usual low play in the system tube, results. Thus, the invention utilizes the recognition that a lug that is bent nonelastically out of a wall of the tube, upon bending back cannot be brought back exactly into its original position, thus the position before the nonelastic deformation. This results from changes in shape of the lug, occurring during the nonelastic deformation, which cannot be eliminated by elastic restoration. These ensure that if outer points of the lug are pressed back to the original level, internal points of the lug are pressed back into the interior space of the system tube, thus project within the level of the inner surface of the system tube, and clamp the cylindrical elements in place there.

Since the tongues are pressed down elastically, upon removing the holder they return toward the outside in their position established by the nonelastic deformation. Thus the cylindrical elements disposed in the system tube, in the absence of the holder, are free and movable with low forces. They can then be easily filled in, adjusted and removed. With the holder in place, the elements are held firmly by the tongues. After removal of the holder, the elements are free again and can be easily removed.

Any suitable objects can be used as holders, for example the thumbs of the person doing the assembly, performing a trial fixation. Advantageously according to claim 2, a sleeve tube that can be slid over is used as a holder, which usually already surrounds the system tube, generally in the form of the so-called fiber tube or in the form of a tube forming the outer surface of the endoscope in the case of a very simple endoscope optical system without illumination.

The nonelastic deformation of the tongues in the direction toward the outside requires a tool that grasps the tongues from the inside. This operation can operate, for example, with a long shaft passing through the tube, for example in the form of a forceps-like design with spreadable jaws and a long shaft. Preferably according to claim 3, however, the system tube has openings located opposite the tongues, through which they can be pressed conveniently and over a short distance, for example with a straight pusher.

A system tube can consist of various materials that are suitable based on their material properties, thus are nonelastically deformable and after this, remain elastically flexible. A number of plastics are suitable for this. Preferably according to claim 4, however, the system tube consists of metal, which has already been proven advantageous for this purpose in endoscope optical systems.

Claims 5 to 7 pertain to advantageous methods for retaining cylindrical elements of an image guide in a system tube of the endoscope.

BRIEF DESCRIPTION OF THE DRAWINGS

In the drawings, the invention is shown by way of example and systematically, in which:

FIG. 1 illustrates a side view of a system tube according to the invention,

FIGS. 2a-2d illustrate sections along line 2-2 in FIG. 1 in various processing steps, and FIG. 3 illustrates a view according to FIG. 1 of a different embodiment.

DETAILED DESCRIPTION

FIG. 1 shows a system tube 1 according to the invention, in the wall of which a tongue 2 with two sections 3 and 4 is cut free. The cuts 3 and 4 according to FIG. 1 are both disposed parallel to the axis of the system tube 1. The tongue 2 remains connected to the system tube 1 at both ends.

FIG. 2a shows a section along line 2-2 in FIG. 1. This section travels exactly through section 3 and shows the tongue 2 viewed from cut 3. An opening 5 in the system tube 1 opposite the tongue 2 is recognizable.

FIG. 2b shows a plunger 6 introduced through the opening 5 into the interior of the system tube 1, which presses the tongue 2 toward the outside when advanced in the direction of the arrow 7. This deformation takes place with fairly high forces, which lead to a nonelastic, thus permanent deformation of the tongue 2, as shown in FIG. 2b. There it is shown that after withdrawal of the plunger 6, the tongue 2 remains in the nonelastically outward-deformed position.

FIG. 2c shows that in the system tube 1 with outwardly deformed tongue 2 according to FIG. 2b, a lens 8, which has a certain smaller dimension compared to the system tube 1, is freely introduced and can be moved for adjustment purposes. The lens 8 is part of the image guide of an endoscope optical system, which is made of cylindrical elements including the lens 8. In addition, the image guide contains more lenses, and in the usual design, also spacing tubes disposed between the lenses to ensure that these are at a certain distance from one another.

The lenses 8 can, as shown, be designed as elongated rod lenses or also as short lenses, in which the problems of tipping are substantially more serious than in the case of long lenses. Instead of individual lenses, lens sets may be provided, which for example may be assembled in a tube.

If a lens 8 according to FIG. 2c is disposed in the system tube 1 adjacent to a tongue 2, it can be retained with the tongue 2 if this is pressed inward against the lens 8. For this purpose the nonelastically outward-deformed tongue 2 is elastically pressed toward the inside from its original position according to FIG. 2c, as shown in FIG. 2d. The holder for pressing the tongue 2 toward the inside in the preferred embodiment according to FIG. 2d may be, for example, a sleeve tube 9 which is designed to closely surround the system tube 1.

This tube 9 is moved relative to the system tube 1. For this purpose in the exemplified embodiment shown it is slid over the system tube 1 in the direction of the arrow 10. It can also remain in place and the system tube be slipped in.

In this process the sleeve tube 9 presses the tongue 2 out of the position according to FIG. 2c toward the inside until the radially outermost point 11 of the tongue 2, which according to FIG. 2c lay outside the otherwise exterior surface of the system tube 1, now lies adjacent to the inner wall of the sleeve tube 9 and thus at the level of the outer surface of the system tube 1, thus at the level at which the point 11 was originally located in the undeformed state of the tongue 2, as shown in FIG. 2a.

As FIG. 2d shows, in the case of this elastic deformation from the position of FIG. 2c into the position of FIG. 2d, the tongue 2 does not go back to its original position according to FIG. 2a. It is already unable to do this since, as shown in FIG. 2c, it has become longer as a result of the nonelastic deformation and no longer fits into its cutout in the system tube 1. It is also nonelastically deformed and thus has permanent deformations that no longer fit into the original form of FIG. 2a. In the exemplified embodiments shown, such permanent deformations especially lie in the area of the outermost point 11.

A necessary result is that the tongue 2, held on the outer circumference of the system tube 1 by its radially farthest outside lying point 11, must now lie with parts inside the inner circumference of the system tube 1, as shown in FIG. 2d. With the points 21 located farthest toward the inside in the exemplified embodiment 2, the tongue 2 consequently lies adjacent to the lens 8 and clamps this firmly with adequately clamping force or at least ensures guidance with low play.

Since the bending of the tongue 2 from the position according to FIG. 2c into the position of FIG. 2d takes place elastically, after removal of the sleeve tube 9 by withdrawal opposite from the direction of the arrow 10 the tongue 2 returns to its position according to FIG. 2c. The lens 8 held by the tongue 2 thus is released and can be easily removed.

Here, elastic bending is also defined as an essentially elastic bending which has nonelastically deforming fractions. The above explanations also apply for this case.

FIG. 3 shows a variant embodiment of system tube 1 of FIG. 1 in the same view. The cutout shapes of the tongues shown are different. In the case of the tongue 12, cut 13 is made such that the tongue is connected to the system tube 1 only at one end. In the case of the tongue 14 the cuts lie parallel to the axis exactly as in the embodiment of FIG. 1, but the cuts 15 are not made as narrow cuts, but as broadly cut-out openings.

A tongue 16 corresponds to the parallel cuts of the embodiment of FIG. 1, but the tongue 16 is divided in the center with a cut 17, so that two independently movable tongues result.

The different tongue shapes shown for example in FIGS. 1 and 3 are all suitable for holding the cylindrical element 8 shown in FIG. 2d. That which is said about FIGS. 2c and 2d also applies analogously here.

In FIGS. 2c and 2d, only one lens 8 is shown in the system tube 1. In the usual endoscope optical system, the system tube 1 is relatively long, and several lenses with spacers located between them are disposed successively in the system tube 1. For each of these cylindrical elements, specific tongues and their assigned, opposite openings may be provided, so that the elements can all be secured individually. Several tongues may also be provided per element in order, for example, to hold both ends of longer elements.

In reference to the longitudinal direction of the system tube 1, the tongues, as shown in FIG. 3 with the tongues 12, 14 and 16, can be located at different positions. However, several tongues may also be disposed in one longitudinal position, for example three tongues at circumferential intervals of 120°, in order for example to achieve a desired three-point support, or two tongues with support of the lens against the system tube as the third point.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

I claim:

1. A system tube of an endoscope optical system, the system tube comprising:
   a cylindrical body having a longitudinal axis and a wall formed around the longitudinal axis of a material capable of being nonelastically deformed, the wall defining an interior and the wall having one or more nonelastically deformed tongues formed by cuts made in the wall, the one or more tongues being deformed in a radially outward direction from the longitudinal axis;
   cylindrical elements of an image guide provided with one or more lenses; and
   a holder disposed over the cylindrical body, the holder having an inner dimension which radially interferes with the one or more tongues such that the one or more tongues are deformed radially inward into the interior to secure the cylindrical elements within the cylindrical body.

2. The system tube according to claim 1, wherein the holder is formed as a sleeve tube wherein the inner dimension is an inner diameter larger than an outer diameter of the cylindrical body and smaller than a cross-sectional dimension of the cylindrical body at a location of the one or more tongues.

3. The system tube according to claim 1, wherein the cylindrical body includes an opening corresponding to each of the one or more tongues, the opening being formed on the wall of the cylindrical body at a position radially opposite to the corresponding one or more tongues.

4. The system tube according to claim 2, wherein the cylindrical body includes an opening corresponding to each of the one or more tongues, the opening being formed on the wall of the cylindrical body at a position radially opposite to the corresponding one or more tongues system.

5. The system tube according to claim 1, wherein the cylindrical body is made of metal.

6. The system tube according to claim 2, wherein the cylindrical body is made of metal.

7. The system tube according to claim 3, wherein the cylindrical body is made of metal.

8. A method for holding cylindrical elements of an image guide provided with one or more lenses in a system tube of an endoscope, the method comprising:
   cutting one or more tongues in a wall of a cylindrical body forming the system tube; and
   nonelastically deforming the tongues in a radially outward direction from a longitudinal axis of the cylindrical body; and
   radially deforming the one or more tongues inward into an interior of the cylindrical body to secure the cylindrical elements within the cylindrical body.

9. The method according to claim 8, wherein the radially deforming comprises sliding a holder over the cylindrical body to provide a radial interference between the one or more tongues and an inner dimension of the holder.

10. The method according to one of claim 8, wherein the nonelastically deforming of the one or more tongues comprises pushing the one or more tongues radially outward from an opening formed on the wall of the cylindrical body at a position radially opposite to the one of more tongues.

11. The method according to one of claim 9, wherein the nonelastically deforming of the one or more tongues comprises pushing the one or more tongues radially outward from an opening formed on the wall of the cylindrical body at a position radially opposite to the one of more tongues.

* * * * *